US00PP10730P

United States Patent [19]

Olesen et al.

[11] Patent Number: Plant 10,730

[45] Date of Patent: Dec. 22, 1998

[54] FLORIBUNDA ROSE PLANT NAMED 'POULCAPE'

[75] Inventors: L. Pernille Olesen; Mogens N. Olesen, both of Fredensborg, Denmark

[73] Assignee: Poulsen Roser ApS, Fredensborg, Denmark

[21] Appl. No.: 864,847

[22] Filed: May 29, 1997

[51] Int. Cl.[6] ..... A01H 5/00

[52] U.S. Cl. ..... Plt./24

[58] Field of Search ..... Plt./22, 24, 26

[56] References Cited

U.S. PATENT DOCUMENTS

P.P. 9,657 10/1996 Zary ..... Plt./24

P.P. 9,688 11/1996 Olesen et al. ..... Plt./26

OTHER PUBLICATIONS

UPOV–ROM, 1997/04, Plant Variety Database, GTI Jouve Retrieval Software, Citation for 'POULcape'.

*Primary Examiner*—Howard J. Locker

[57] ABSTRACT

A new, repeat flowering, light yellow floribunda rose plant which has abundant flowers, good keepablility and dark glossy green foliage. The variety successfully propagates from softwood cuttings and budding is suitable for year round production in commercial glasshouses. This new and distinct variety has shown to be uniform and stable in the resulting generations from such asexual propagation.

2 Drawing Sheets

SUMMARY OF THE INVENTION

The present invention constitutes a new and distinct variety of floribunda rose plant which originated from a controlled crossing between 'MACrexy' and an unnamed seedling. The new rose may be distinguished from its seed parent by the following combination of characteristics: 'MACrexy' is a clear pink floribunda rose shown and described in U.S. Plant Pat. No. 6,713. The new rose has a light yellow flower and has superior disease resistance to mildew and rust in outdoor culture. The new rose may be distinguished from its pollen parent (an unnamed seedling) as said pollen parent is a compact floribunda with flower color of Red Group 56B, while the new rose has a light yellow bloom. The two parents were crossed in the summer of 1989 and the resulting seed was planted in December of 1989 in a controlled environment. The new variety is named 'POULcape'. The objective of the hybridization of this rose variety for commercial culture was to create a new and distinct variety with:

1. Uniform and abundant flowers with good keepability and shipability;

2. Attractive long lasting foliage and compact growth,

3. Year-round flowering under glasshouse and nursery conditions;

4. Suitability for production from softwood cuttings in pots;

5. Durable flowers and foliage which make a variety suitable for distribution in the floral and nursery industry.

This combination of qualities was not present in previously available commercial cultivars of this type and distinguish 'POULcape' from all other varieties of which we are aware.

The seeds from the hybridization were germinated in the spring of 1990 and evaluations were conducted on the resulting rose plants throughout the summer of 1990 in a controlled environment. 'POULcape' was selected by L. Pernille and Mogens N. Olesen in their rose development program in Fredensborg, Denmark in June, 1990. Asexual reproduction of 'POULcape' by cuttings and traditional budding was first done by L. Pernille and Mogens N. Olsen in August, 1990. This initial and subsequent propagations have demostrated that the characteristics of 'POULcape' are true to type and are transmitted from one generation to the next.

BRIEF DESCRIPTION OF THE DRAWINGS

The accompanying color illustrations show as true as is reasonably possible to obtain in color photographs of this type, the typical characteristics of the buds, flowers, leaves, stems, and a plant of 'POULcape'. Specifically illustrated in SHEET1: 1. Stem or entire plant showing branching and the attachment of leaves, buds, and peduncles; 2. Flower bud, partially opened bud, and open bloom; 3. Flower petals, detached; 4. Sepals, receptacle, and pedicel; 5. Flowering stem as well as a bare stem exhibiting thorns; 6. Leaves.

Specifically illustrated in SHEET 2 are flower buds and blooms in greater detail.

DETAILED DESCRIPTION OF THE VARIETY

The following is a detailed description of 'POULcape', as observed in its growth in glasshouses in Fredensborg, Denmark and Half Moon Bay, Calif. and in field nursery in Applegate, Oregon. Descriptions were made from plants treated with growth regulators normally used in the greenhouse production process. The growth regulator Paclobutrazol was applied at 30 ppm weekly for three weeks beginning at a plant age of 10 weeks. The peduncle lengths mentioned may actually be shorter and the foliage color several shades darker than on untreated specimens. Color references are made using The Royal Horticultural Society (London, England) Colour Chart, 1995.

For a comparison, the nearest existing rose variety is POULrek, a patented variety described and illustrated in U.S. Plant Pat. No. 9,688 and issued on Nov. 12, 1996. Chart 1 details several physical charateristics of 'POULcape' and 'POULrek'.

CHART 1

| | 'POULcape' | 'POULrek' |
|---|---|---|
| Upper side of petal surface | RHS 10 D of the Yellow Color Group | RHS 36 D of the Red Color Group |
| Reverse side of petal surface | RHS 4 D of the Yellow Color Group | RHS 36 D of the Red Color Group |
| Color of thorns/ prickles when young | RHS 143 D of the the Green Color Group | RHS 48 C of the Red Color Group |

Parents: MACrexy×Unnamed Seedling.
Classification:
*Bontanical.*—*Rosa hybrida.*
*Commercial.*—Floribunda.

Flower And Flower Bud

Blooming cycle: Recurrent.
Flower bud:
*Size.*—25–30 mm in length when petals are just beginning to crack open.
*Bud form.*—Pointed.
*Bud color.*—R.H.S. 10 D of the Yellow Color Group at ¼ opening.
*Sepals.*—R.H.S. 144 B of the Green Group. A limited number of foliaceous appendages generally present. Surfaces of sepals moderately pubescent. Stiff hairs present on exterior of sepal.
*Peduncle.*—Surface: Smooth, with stiff hairs. Length: 35–45 mm average length. Color: R.H.S. 144 B of the Green Group. Prickles: Few to none.
*Receptacle.*—Surface: Smooth, glabrous. Shape: Urn-shaped. Size: Medium, 6 mm×7 mm. Color: R.H.S. 144 B of the Green Group.
*Borne.*—On greenhouse plants, one to four buds per flowering stem. On plants growing outdoors, eight to fifteen buds per flowering stem.
Flower bloom:
*Diameter.*—Medium. 55–65 mm on average.
*Form.*—Upon opening, pointed. Completely open convex, with petals reflexing.
*Petalage.*—Double. Average range: 50–60 petals. Petaloids few, approx. 6–8. Small. Yellow Group 10 C.
*Color.*—Upon opening, the upper surface is R.H.S. 10 D of the Yellow Color Group. Upon opening, the reverse side is R.H.S. 4 D of the Yellow Color Group. After opening, the upper surface is R.H.S. 10 D of the Yellow Color Group. After opening, the reverse surface is R.H.S. 4 D of the Yellow Color Group. A small petal spot R.H.S. 3 C of the Yellow Group exists on the inner side of the petal base. A small petal spot R.H.S. 3 C of the Yellow Group exists on the outer side of the petal base.
*Reflex.*—Petals reflex backwards upon opening. *Variations.*—Center petals darker yellow. Yellow Group 10B to Yellow Group 10C. *Fragrance.*—Lightly fragrant. *Duration.*—8–11 days as a cut flower and 10–14 days on the plant.

Reproductive organs:
*Pollen.*—Golden yellow.
*Anthers.*—Size: Medium. Color: Golden yellow.
*Filaments.*—Color: Yellow green.
*Stigmas.*—Location slightly superior to anthers.
*Styles.*—Color: Yellow green.
Plant growth:
Vigorous, compact, and bushy. When grown as a 15 cm pot plant, the average height of the plant itself is 25–30 cm and the average width is 20–25 cm. When grown as a nursery plant on its own roots the average plant height is 50–60 cm and the average plant width is 50–60 cm.
Stems:
Color.—Young wood: Green Group 143C. Older Wood: Green Group 138C.
*Thorns.*—Incidence: Few to moderate thorns. Size: Average length: 5–7 mm. Color: Yellow Group 145D with intonation of Red Group 50B. Shape: Concave to linear.
*Bark.*—Young Wood: Smooth Yellow Green Group 145B. Older Wood: Smooth Flowering stems 25–35 cm Green Group 139B.
Plant foliage:
*Normal number of leaflets on average leaves.*—5–7 leaflets.
*Leaf size.*—Medium. 50 mm×90 mm.
*Abundance.*—Abundant. p2*Color, mature foliage.*—Upper leaf surface: Dark green. R.H.S. 139 A of the Green Color Group. Bottom: Medium green. R.H.S. 138 A of the Green Color Group.
*Juvenile foliage.*—Upper surface of leaflets Green Group 138A with leaflet margins, petioles, stipules, and upper surfaces of rachis having a red intonation of 178B to 178C. Lower surface of leaflets Green Group 138B.
Plant leaves and leaflets:
*Stipules.*—Present. 10–15 mm in length. Green Group 138A.
*Petiole.*—Length: 20–25 mm. Underneath: With prickles.
*Color.*—Green Group 138A. Under high light conditions a red intonation of Greyed-Red Group 178C.
*Edge.*—Finely serrated.
*Shape.*—Leaflets are ovate.
*Leaflets.*—Number: 5–7.
*Rachis.*—Green Group 138A. Under high light conditions a red intonation of Greyed-Red Goup 178C.
*Other.*—Moderately Glossy with thick texture.
Disease resistance: Resistance to mildew, black spot, and Botrytis under normal growing conditions in Half Moon Bay, Calif. and Fredensborg, Denmark.
We claim:
1. A new and distinct variety of rose plant of the floribunda class, substantially as herein illustrated and described, as a distinct and novel rose variety due to its abundant light yellow flowers with good keepability, attractive long lasting foliage, even compact growth habit, year round flowering under glasshouse conditions, suitability for production from softwood cuttings in pots, durable flowers which make the variety suitable for distribution in the floral and nursery industry.

* * * * *

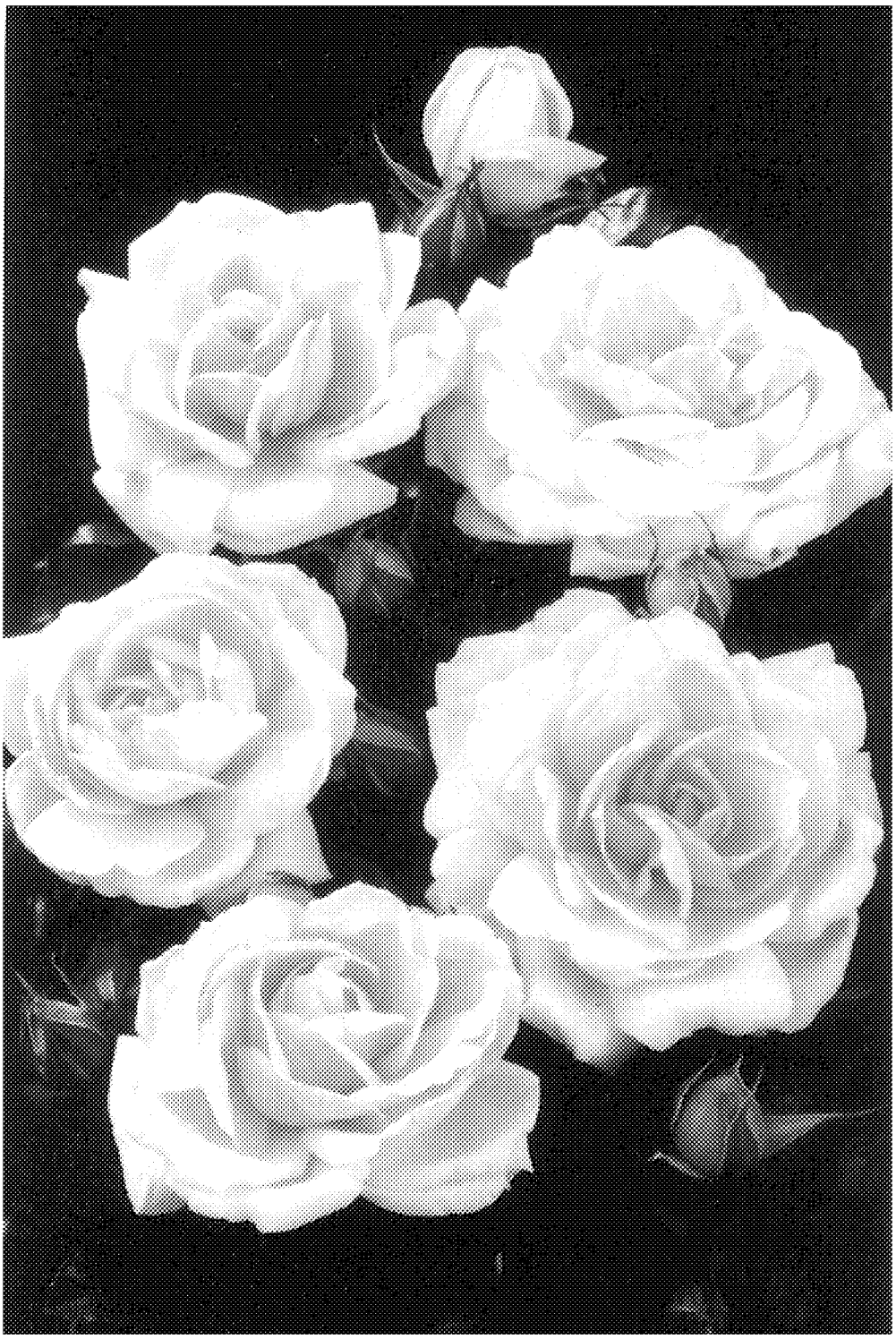

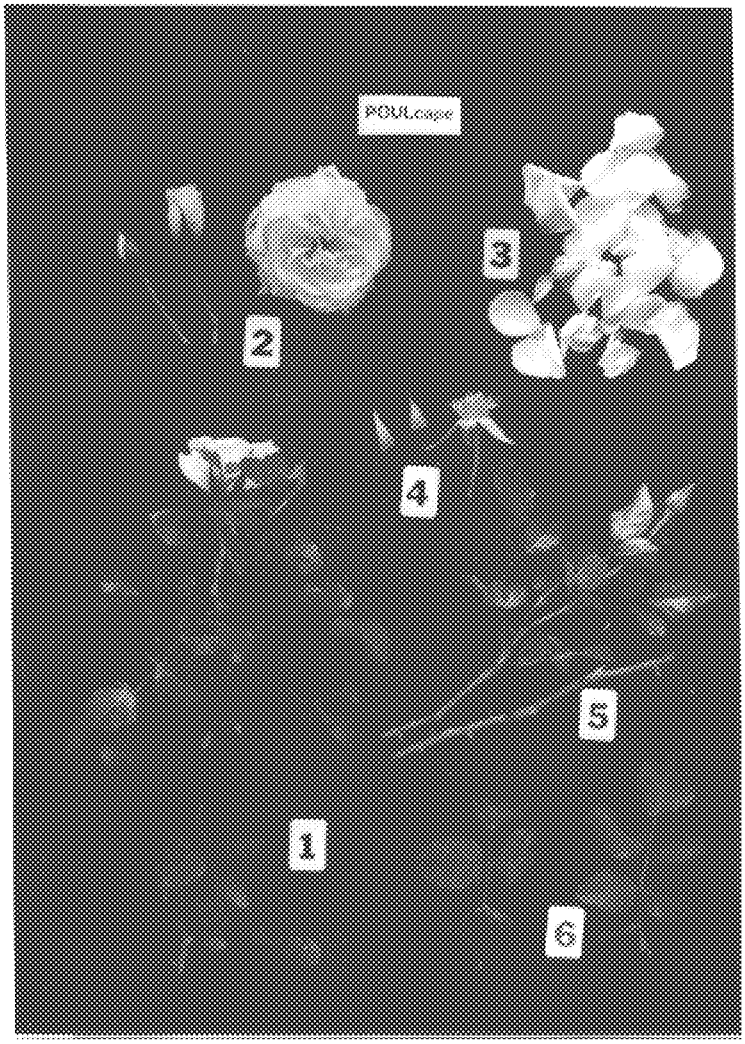
POUL.cage
1
2
3
4
5
6